United States Patent [19]

Foster

[11] 4,408,081
[45] Oct. 4, 1983

[54] PROCESS FOR OXIDATION OF ISOBUTANE

[75] Inventor: Elton G. Foster, Houston, Tex.

[73] Assignee: Shell Oil Company, Houston, Tex.

[21] Appl. No.: 308,629

[22] Filed: Oct. 5, 1981

[51] Int. Cl.³ .......................................... C07C 179/02
[52] U.S. Cl. ..................................... 568/571; 568/565
[58] Field of Search ................................ 568/571, 565

[56] References Cited

U.S. PATENT DOCUMENTS

| | | |
|---|---|---|
| 2,845,461 | 7/1958 | Winkler et al. ...................... 568/571 |
| 3,478,108 | 11/1969 | Grane ................................... 568/571 |
| 3,502,740 | 11/1970 | Zapacek et al. ...................... 568/571 |
| 3,816,540 | 6/1974 | Barone et al. ......................... 568/571 |
| 3,855,314 | 12/1974 | Dubois et al. ........................ 568/571 |
| 3,907,902 | 9/1975 | Grane ................................... 568/571 |
| 3,974,228 | 8/1975 | Barone ................................. 568/571 |
| 4,128,587 | 5/1978 | Jubin .................................... 568/571 |

FOREIGN PATENT DOCUMENTS 7709269  5/1978  Netherlands ........................ 568/571

OTHER PUBLICATIONS

Winkler, "Industrial and Engr. Chem.", vol. 53 (1961), p. 655.

*Primary Examiner*—Werren B. Lone
*Attorney, Agent, or Firm*—Richard F. Lemuth

[57] ABSTRACT

In continuous preparation of tertiary-butyl hydroperoxide by the direct oxidation of isobutane in dense-phase reaction mixture at a pressure in excess of the critical pressure of the mixture, and under conditions relating to temperature and to oxygen and isobutane content of the mixture, improvement in selectivity to TBHP is realized by a process which comprises conducting a plurality of such oxidation reactions each in one of a series of dense-phase reaction mixtures by continuously introducing isobutane reactant into the first reaction mixture in the series, continuously introducing oxygen reactant into each reaction mixture of the series, and withdrawing a continuous flow from each mixture of the series and introducing this flow into the next mixture of the series, with the provision that the continuous flow withdrawn from the last mixture of the series is taken from the process as a TBHP-containing product mixture characterized by a conversion of the isobutane reactant of between about 3 and 25 percent.

9 Claims, 2 Drawing Figures

PROCESS FOR OXIDATION OF ISOBUTANE

BACKGROUND OF THE INVENTION

This invention relates to an improved process for the production of tertiary-butyl hydroperoxide by direct oxidation of isobutane. More particularly, this invention relates to a continuous oxidation process carried out in a series of reaction zones each maintained as a single dense phase.

Tertiary-butyl hydroperoxide (hereinafter sometimes referred to as TBHP) is a material of commerce having application as a catalyst, as an intiator for free radical-type reactions and as a starting material or intermediate in the production of valuable chemicals such as oxirane compounds and other organic hydroperoxides.

Because of the ready availability and low cost of starting materials, significant effort has been focused in the past specifically on the preparation of TBHP by direct oxidation of isobutane. It is known that this reaction can be conducted in the vapor phase in the presence of an added catalyst, e.g., hydrogen bromide, or in the liquid phase of a vapor-liquid mixture with or without a catalyst, for instance, according to the teachings of Winkler et al (U.S. Pat. No. 2,845,461, and the publication "Liquid Phase Oxidation of Isobutane", Industrial and Engineering Chemistry, vol. 53 (August, 1961), p. 655), Grane et al (U.S. Pat. Nos. 3,478,108 and 3,907,902) and/or Barone et al (U.S. Pat. No. 3,816,540). It has further been found, as described in the commonly-assigned, copending application of E. G. Foster and E. F. Lutz, entitled Oxidation of Isobutane under Supercritical Conditions, Ser. No. 308,631, filed on even date herewith, that the reaction can be carried out in a supercritical reaction mixture at a temperature above the critical temperature of the mixture, at a pressure above the critical pressure of the mixture, and under conditions relating to composition of the mixture. Although the supercritical phase reactoin process offers substantial advantage over the prior art liquid-phase or vapor-phase methods for isobutane oxidation, the production of TBHP by direct oxidation under any of the known processes, an inverse relationship exists between selectivity and conversion in the isobutane oxidation reaction, so that an increase in one is generally obtained only at the expense of a decrease in the other.

SUMMARY OF THE INVENTION

It has now been found that in the preparation of tertiary-butyl hydroperoxide by a process which comprises the direct reaction of isobutane with molecular oxygen an improvement providing enhanced process selectivity to TBHP without sacrifice in isobutane conversion comprises the steps of (a) conducting a plurality of essentially steady-state isobutane oxidation reactions, each reaction in one of a series of reaction zones, each zone containing an agitated dense-phase reaction mixture, (b) introducing a continuous flow of isobutane into the mixture of the first reaction zone in the series, (c) introducing a continuous flow of oxygen into the mixture of each reaction zone of the series, (d) withdrawing a continuous flow of reaction mixture from each zone of the series and (e) introducing this withdrawn flow into the reaction mixture of the next zone of the series, with the provision that the flow withdrawn from the last zone of the series is taken from the process as a tertiary-butyl hydroperoxide containing product mixture characterized by a conversion of isobutane of between about 3 and 25 percent. A dense-phase reaction mixture is one maintained at a pressure above its critical pressure and at a temperature sufficiently elevated so that the reaction mixture behaves like a single, dense, quasi-liquid phase. (Suitable temperatures are in the range of 140° to 170° C.). In other words, the dense-phase reaction mixture is free of the vapor phase which has been characteristic of prior art reaction in the vapor phase or in a two phase (vapor-liquid) mixture. Preferably, the reaction mixture of at least the first reaction zone is a supercritical mixture, that is, a mixture comprising isobutane and oxygen reactants, and tertiary-butyl hydroperoxide, tertiary-butyl alcohol, and other reaction products, said mixture maintained above its critical temperature as well as above its critical pressure. Each dense-phase reaction mixture of the series is defined as containing a quantity of isobutane such that the partial density of isobutane in the mixture is at least about 12 lb/ft$^3$, and as containing oxygen in a concentration between about 0.005 and 5 percent by mol. The oxygen is present in solution in the dense-phase mixture, and not as a separate vapor phase.

The improvement in TBHP preparation which is realized by practice in accordance with the invention is primarily in the nature of enhanced oxidation reaction selectivity to TBHP at a given conversion of isobutane. In preferred embodiments, this improvement is a valuable complement to the general benefits of supercritical phase isobutane oxidation with respect to enhanced production of TBHP per unit of reactor volume per unit of reaction time, as are described in the afore-mentioned copending application.

Practical advantage may be taken of the improvement provided by the invention in any one or more of a number of ways. For instance, direct application may be made of the invention to provide isobutane oxidation with a selectivity of TBHP not heretofore possible. Alternatively, oxidation may be carried out to produce a reaction mixture having an enhanced level of isobutane conversion for a given selectivity, thus simplifying downstream processing of the product mixture.

DESCRIPTION OF THE PREFERRED EMBODIMENTS

Figure 1:
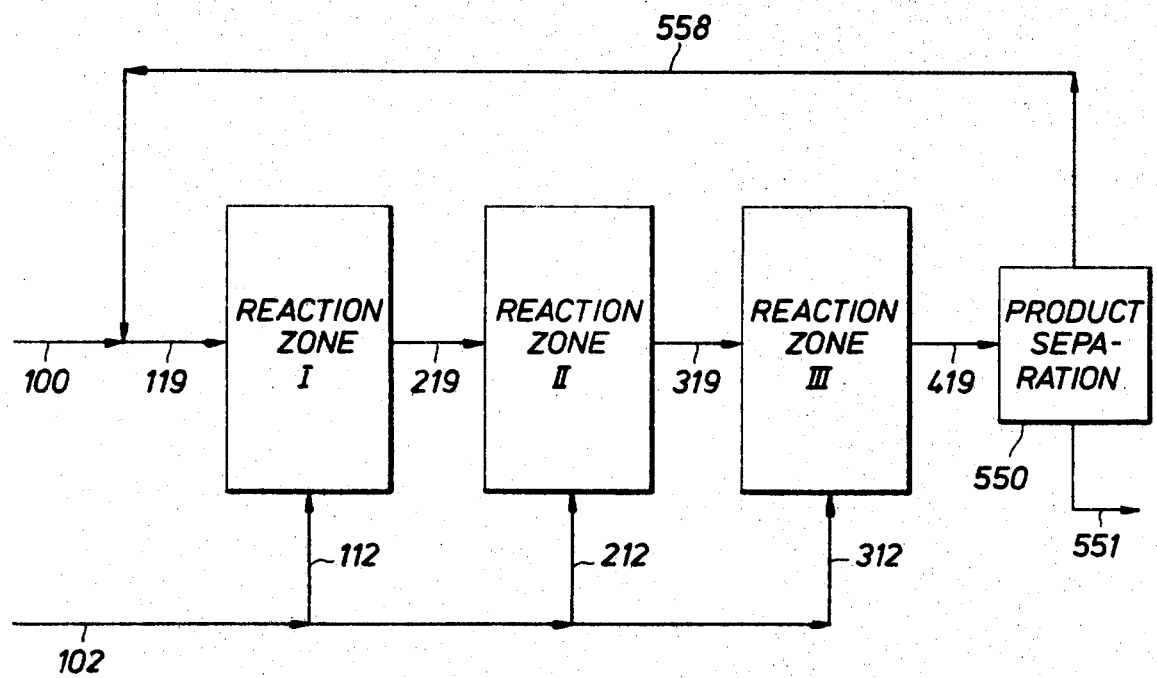

A necessary characteristic of the process of the invention is a series of isobutane oxidation reactions conducted in a series of corresponding reaction zones. For purposes of the invention, each of such reactions is conducted in a mixture under dense-phase conditions, that is, at a pressure above the critical pressure of the mixture and under specified temperature, so that the mixture behaves as a single, dense, quasi-liquid phase. Preferably, for purposes of the invention the dense-phase reaction mixture pressure is greater than about 700 psig, while a pressure in the range of about 800 to 1800 psig is preferred, and a pressure in the range of about 900 and 1500 psig is considered most preferred.

Reaction temperature in each of the several dense-phase reaction zones of the process of the invention is suitably in the range of about 140° to 170° C., while preference is given to a temperature in the range of about 145° to 165° C. A temperature of about 150° to 160° C. is most preferred.

Efficient dense-phase isobutane oxidation further requires the presence in each mixture of a quantity of isobutane sufficient to provide a partial density of isobutane (defined as the weight of isobutane reactant per unit volume of reaction mixture) that is greater than about 12 lb/ft$^3$. Preferably, isobutane partial density in the reaction mixture is between about 15 and 35 lb/ft$^3$, while the range from about 18 to 30 lb/ft$^3$ is more preferred and the range from about 19 to 25 lb/ft$^3$ is considered most preferred.

Oxygen concentration in the reaction mixture is also an important factor, with a concentration in the range of about 0.005 to 5 percent by mol (%m) being preferred. To accomplish TBHP production at a relatively fast rate, an oxygen concentration in the range of about 0.1 to 3.5% m is generally more preferred. Isobutane oxidation is, however, also very suitably conducted at lower oxygen concentration, i.e., from about 0.005 to 0.1% m. As reported in the commonly-assigned, co-pending application of H. J. baumgartner, entitled Oxidation of Isobutane in the Dense Phase at Low Oxygen Concentration, Ser. No. 308,630, filed on even date herewith, oxidation at low oxygen concentration is itself characterized by enhanced selectivity for TBHP. The teachings of the Baumgartner application are herein incorporated by reference. Since the effects of the process of this invention and the process described in the Baumgartner application are cumulative with respect to selectivity enhancement, there is advantage in carrying out isobutane oxidation in accordance wiht the teachings of both, although this will entail some sacrifice in TBHP production rate.

The above specified reaction mixture parameters for purposes of this invention are generally the same as those specified for the process of Foster and Lutz described in their above-referenced application. The invention of the Foster and Lutz application further calls for isobutane oxidation to be conducted (at least in part) in the supercritical phase, i.e., at a reaction temperature that is greater than the critical temperature of the reaction mixture. For purposes of this invention, it is preferred, although not necessary, that the process be conducted to some extent in such a supercritical phase. Specifically, it is preferred that the reaction mixture of at least the first reaction zone of the invention be maintained at a reaction temperature in excess of the mixture's critical temperature. (The teachings of the Foster and Lutz application on dense- and supercritical-phase isobutane oxidation are herein incorporated by reference.)

The instant invention is considered to relate in essence to process steps for the operation of a plurality of such dense-phase reaction mixtures to accomplish enhanced TBHP selectivity without sacrifice in isobutane conversion. While the number of dense-phase reaction mixtures (and reaction zones) is not critical, it may generally be said, on the basis of process economics and practical operation, that a number of zones from 2 to 8, inclusive, is preferred, from 2 to 6, inclusive, is more preferred, and from 2 to 4, inclusive, is most preferred. During the continuous TBHP preparation process of the invention, essentially steady-state conditions are maintained in each of the multiple zones by introduction of a continuous flow of isobutane reactant into the reaction mixture of the first zone of the series, introduction of a continuous flow of oxygen reactant to the reaction mixture of each zone of the series, withdrawal from each zone of a continuous flow of the reaction mixture therein, and introduction of this withdrawn continuous flow to the mixture of the next zone of the series, with provision made for taking the flow of mixture withdrawn from the last zone as reaction product. Isobutane reactant is suitably substantially pure isobutane, i.e., substantially free of other hydrocarbons and metal ion contaminants. The oxygen reactant is preferably substantially pure oxygen, as is available from a variety of commercial sources. Most preferably, the substantially pure isobutane reactant is introduced only into the first zone of the series. Isobutane is then supplied to subsequent reaction zones only as a part of the reaction mixture that is withdrawn from one zone and transferred to the next. Introduction of any of the substantially pure isobutane reactant flow into any reaction zone subsequent to the first is detrimental to the process object of enhanced selectivity for TBHP. However, advantages associated with the invention are still to be realized so long as the major part of the isobutane reactant introduced into the process is introduced into the first reaction zone of the series. Preferably, substantially all of the isobutane reactant supplied to the process is introduced into the first zone.

Introduction is made of these reactants into the reaction mixtures of the various reaction zones as indicated at pressures and at rates sufficient to maintain the specified conditions of isobutane partial density and oxygen concentration in each zone of the series. Consideration is necessarily given to conversion of isobutane in each of the zones; for instance, when the isobutane reactant is introduced into only the first zone of the series, the quantity so introduced and the pressure must be sufficient to provide the minimum desired isobutane partial density in the last zone of the series. The continuous flows of reaction mixture withdrawn from each zone of the series and introduced into the next zone, or in the case of the last zone taken as product, have rates which individually maintain essentially steady state, dense-phase operation in each zone and overall provide in the process product the specified 3 to 25% conversion of isobutane. While some advantages of enhanced selectivity for TBHP are realized outside of the 3 to 25% isobutane conversion range specified as suitable for the process of the invention, the nature of the relationships between isobutane oxidation rate, conversion and selectivity is such that operation of multiple reaction zones according to the invention outside of this range is not considered to be of great practical benefit. Preferably, overall conversion of isobutane reactant during the process of the invention is limited to the range from about 5 to 20%; more preferably, this conversion is maintained between about 7 and 15%; operation with a conversion of about 10% in the reaction mixture taken from the last zone of the series is considered most preferred.

The process of the invention and particular equipment suitable for use in its practice are now illustrated by reference to the attached drawing.

FIG. 1 of the drawing depicts the process in schematic flow diagram fashion, indicating process flows introduced into and withdrawn from the several reaction zones.

Figure 2:
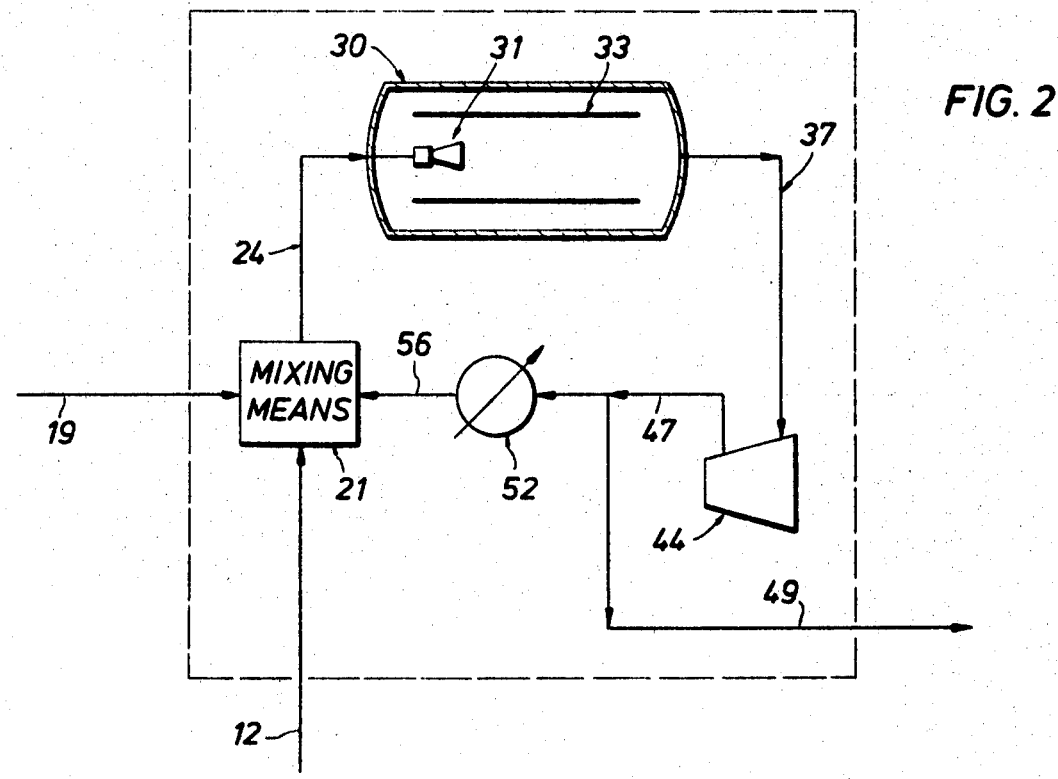

FIG. 2 describes a preferred arrangement of processing equipment within each zone. The specific illustrations provided by these figures are intended to provide description of a narrow embodiment of the invention and not to be construed to limit its broader scope.

With particular reference to FIG. 1, there is depicted a series of three dense-phase reaction zones: a first zone (designated I), a second zone (II), and a third zone (III). A continuous supply of substantially pure isobutane reactant is provided for purposes of the process from an external source via line 100. Similarly, a continuous supply of a suitable oxygen reactant is provided via line 102. Since the process of the invention is intended to accomplish a limited conversion of isobutane, it is preferable that provision be made for recovery of unreacted isobutane from the product mixture of the overall process and for recycle of this recovered isobutane to further oxidation reaction. In the process embodiment shown, such an isobutane recycle stream is designated 558. Steams 558 and 100 are combined to yield an isobutane flow that is introduced only into the first reaction zone via line 119. A portion of the oxygen supply is also introduced, via line 112, into zone I.

Zone I comprises an agitated oxidation reaction mixture. The isobutane and oxygen introduced into this zone are introduced into this mixture and therein contacted in the dense phase for reaction to TBHP. Preferably, the reaction in this first zone is conducted at a temperature greater than the critical temperature of the reaction mixture therein, and at a pressure sufficient to maintain an isobutane partial density of at least 12 lb/cu. ft. The reaction mixture of zone I is typically characterized by a conversion of between about 0.1 to 5% of the isobutane introduced thereto. A flow of the reaction mixture of zone I is continuously withdrawn and introduced via line 219 into zone II. Also introduced into this second zone, via line 212, is a portion of the process oxygen supply. Zone II comprises an agitated dense-phase oxidation reaction mixture into which the flows of the first zone mixture 219 and oxygen 212 are introduced for contact and further oxidation to TBHP. The reaction mixture of zone II is characterized by a level of isobutane conversion that is greater than that of the reaction mixture of the first zone and typically is in the range of about 1 to 10%. A flow of the reaction mixture of zone II is continuously withdrawn, and introduced via line 319 into reaction zone III, which also receives a continuous flow of oxygen reactant via line 312.

Zone III comprises an agitated dense-plate reaction mixture into which the flows of second zone reaction mixture 319 and oxygen 312 are introduced for reaction in part to TBHP. This last reaction mixture of the series is characterized by an isobutane conversion greater than that of the second zone, and necessarily between about 3 and 25%. A flow of this mixture is continuously withdrawn, via line 419, as the TBHP-containing product mixture of the invention. In an optional feature of the process embodiment illustrated by FIG. 1, this flow of product mixture 419 is separated in a separation means 550, for instance a generally conventional distillation means, to yield a TBHP-rich stream 551, containing for example between about 25 and 50 percent by weight TBHP, and an isobutane-rich stream 558 suitable for recycle to the first reaction zone. Further treatment of stream 551 to recover a purified TBHP product may be accomplished by methods well known to the art.

FIG. 2 illustrates a reaction zone preferred for use in the process of the invention, and specifically depicts a suitable disposition of a dense-phase reaction mixture within the zone together with a typical arrangement of associated processing equipment. This Figure, like FIG. 1, is intended as a schematic representation and does not purport to show the details of equipment, instrumentation, valving, and the like, as such matters will be apparent to those of skill in the art.

Referring to FIG. 2 there is shown the introduction into the zone of an isobutane-containing flow 19 and an oxygen reactant stream 12. Since the zone depicted is suitable for use as any one of the series of several zones called for by the invention, the flow 19 may be the substantially pure isobutane feed, e.g., stream 119 in FIG. 1, if the zone is considered the first of the series, or alternatively the flow of reaction mixture withdrawn from a previous zone in the series, e.g., stream 219 or 319 in FIG. 1. To facilitate a preferred thorough mixture of streams 12 and 19 into the reaction mixture, these streams are here passed together with a circulating flow of reaction mixture 56 through a mixing means 21, suitably a mixing nozzle of conventional design. The mixed flow 24 is then routed via eductor 31 to reactor 30, containing dense-phase reaction mixture. Agitation and cooling of the reaction mixture are both facilitated, in the embodiment shown by the circulating flow of the mixture external to the reactor. A flow 37 of reaction mixture is taken from reactor 30 by pumping means 44 for circulation through line 47 to heat exchange 52. Cooled mixture 56 is introduced into the mixing means 21 for combination with streams 12 and 19 and eventual routing back to reactor 30 through eductor 31. Flow through this eductor, together with the action of a draft tube 33 positioned within the reactor, produces a high degree of mixing within the dense-phase reaction mixture. A continuous flow of the reaction mixture is taken from line 47 downstream of the pumping means. This flow is withdrawn from the zone and either introduced into the next zone of the series or, in the case that the zone depicted is the last zone of a series; taken as product mixture.

It will be understood by those skilled in the chemical processing arts that while such specific items of processing equipment as are shown in the reaction zone of FIG. 2 may be preferred, they are for the most part not critical to the practice of the process of the invention. It is only necessary in terms of processing equipment that the zone provides a reactor for containing the reaction mixture, means for agitating the mixture, and means for controlling temperature within the range specified by cooling the mixture to remove heat generated in the exothermic reaction.

Illustrative Embodiment

Illustration is now provided of the results of TBHP preparation under the process of the invention, particularly in terms of the influence of practice under the invention upon the relationship between isobutane conversion and reaction selectivity to TBHP. Comparison is also made of such results to the performance of a continuous isobutane oxidation process not in accordance with the invention.

For purposes of this illustration, consideration is given to TBHP preparation by isobutane oxidation carried out under the process steps of the invention in multiple (two or three) equal volume reaction zones, as well as to continuous isobutane oxidation in a single reaction mixture. Each reaction mixture is maintained as a single dense phase at a temperature of 150° C. and a pressure of 1000 psig. Oxygen addition to each mixture is regulated to provide a concentration therein of 1%m. Isobutane is fed to the single zone process reactor or to the first reactor of the multiple zone embodiments at that rate which results in the desired level of isobutane conversion in the product. Pressure is controlled by controlling the rate of product withdrawal from the single zone or from the last zone of the multiple zone embodiments.

The following table presents results that are representative of those which would be obtained through operation in accordance with these two and three reaction zone process embodiments and the single zone comparative reaction. Process selectivity to TBHP, expressed as a percentage by mol (%m), and calculated on the basis of mols of TBHP produced per mols of isobutane converted, for operation with the single zone (I), two zones (II), and three zones (III) are tabulated at each of several common overall process isobutane conversion values to illustrate the improvement associated with the invention.

TABLE

| Isobutane | Selectivity to TBHP, % m | | |
|---|---|---|---|
| Conversion | I | II | III |
| 3% | 65.6 | 69.6 | 71.3 |
| 5% | 61.5 | 65.7 | 67.6 |
| 10% | 51.6 | 56.0 | 58.0 |
| 15% | 43.0 | 47.9 | 50.2 |
| 20% | 36.0 | 41.0 | 43.4 |
| 25% | 29.9 | 34.9 | 37.3 |

I claim as my invention:

1. In the preparation of tertiary-butyl hydroperoxide by the direct oxidation of isobutane in dense-phase reaction mixture at a reaction temperature in the range from about 140° C. to 170° C. and at a reaction pressure in excess of the critical pressure of the mixture and greater than about 700 psig, the improvement which comprises the steps of:
 (a) conducting a plurality of essentially steady-state isobutane oxidation reactions, each reaction in one of a series of reaction zones, each zone containing an agitated dense-phase oxidation reaction mixture,
 (b) introducing a continuous flow of isobutane reactant into the mixture of the first zone of the series,
 (c) introducing a continuous flow of oxygen reactant into the mixture of each zone of the series,
 (d) withdrawing continuous flows of reaction mixture from each zone of the series, and
 (e) introducing each of the withdrawn flows into the mixture of the zone that is next subsequent to the one from which it is withdrawn, with the provision that the flow withdrawn from the last zone of the series is taken from the process as a tertiary-butyl hydroperoxide containing product mixture characterized by a conversion of isobutane of between about 3 and 25 percent.

2. The process of claim 1, wherein the reaction mixture of each zone: (i) contains isobutane in a partial density between about 15 and 35 $lb/ft^3$, (ii) contains oxygen in a concentration between about 0.005 and 5 percent by mol, (iii) has a temperature between about 140° and 170° C., and (iv) has a pressure greater than about 800 psig.

3. The process of claim 1, wherein the essentially steady-state oxidation reactions are conducted in a series of from 2 to 8 reaction zones, and wherein the reaction mixture of each zone: (i) contains isobutane in a partial density between about 18 and 30 $lb/ft^3$, (ii) contains oxygen in a concentration between about 0.005 and 5 percent by mol, (iii) has a temperature between about 145° and 165° C., and (iv) has a pressure greater than about 800 psig.

4. The process of claim 1, wherein the essentially steady-state oxidation reactions are conducted in a series of from 2 to 6 reaction zones, and wherein the reaction mixture of each zone: (i) contains isobutane in a partial density between about 19 and 25 $lb/ft^3$, (ii) contains oxygen in a concentration between about 0.005 and 5 percent by mol, (iii) has a temperature between about 150° and 160° C., and (iv) has a pressure between about 900 and 1500 psig.

5. The process of claim 4, wherein the essentially steady-state oxidation reactions are conducted in a series of from 2 to 4 reaction zones.

6. The process of claim 2 or claim 3, wherein the product mixture is characterized by a conversion of isobutane between about 5 and 20 percent.

7. The process of claim 3 or claim 4, wherein the product mixture is characterized by a conversion of isobutane between about 7 and 15 percent.

8. The process of claim 5, wherein the oxygen concentration in the reaction mixture of each zone is between about 0.1 and 3.5 percent by mol, and wherein the product mixture is characterized by a conversion of isobutane of about 10 percent.

9. The process of claim 1, 2, 3, 4 or 8, wherein the temperature of the reaction mixture of the first reaction zone of the series is in excess of the critical temperature of the mixture.

* * * * *

REEXAMINATION CERTIFICATE (506th)
United States Patent [19]
Foster et al.

[11] B1 4,408,081
[45] Certificate Issued  * May 13, 1986

[54] PROCESS FOR OXIDATION OF ISOBUTANE

[75] Inventors: Elton G. Foster; Eugene F. Lutz, both of Houston, Tex.

[73] Assignee: Shell Oil Company, Houston, Tex.

Reexamination Request:
No. 90/000,753, Apr. 9, 1985

Reexamination Certificate for:
Patent No.: 4,408,081
Issued: Oct. 4, 1983
Appl. No.: 308,629
Filed: Oct. 5, 1981

[*] Notice: The portion of the term of this patent subsequent to Sep. 13, 2000 has been disclaimed.

[51] Int. Cl.[4] ............................................. C07C 179/02
[52] U.S. Cl. ..................................... 568/571; 568/565; 568/569
[58] Field of Search ..................... 568/565, 569, 571

[56] References Cited

U.S. PATENT DOCUMENTS

| | | | |
|---|---|---|---|
| 2,845,461 | 7/1958 | Winkler et al. | 568/571 |
| 3,478,108 | 11/1969 | Grane | 568/571 |
| 3,502,740 | 3/1970 | Zajacek et al. | 568/571 |
| 3,816,540 | 6/1974 | Barone et al. | 568/571 |
| 3,855,314 | 12/1974 | Dubois et al. | 568/571 |
| 3,907,902 | 9/1975 | Grane | 568/571 |
| 3,974,228 | 8/1976 | Barone | 568/571 |
| 4,002,687 | 1/1977 | D'Aubigne et al. | 568/571 |
| 4,066,706 | 1/1978 | Schmidt | 568/571 |
| 4,128,587 | 12/1978 | Jubin | 568/571 |
| 4,404,406 | 9/1983 | Lutz et al. | 568/571 |
| 4,408,081 | 10/1983 | Foster | 568/571 |

FOREIGN PATENT DOCUMENTS

7709269  5/1978  Netherlands ................... 568/571 X

OTHER PUBLICATIONS

Winkler "Industrial and Engr. Chem.", vol. 53 (1961), p. 655.

*Primary Examiner*—Werren B. Lone

[57] ABSTRACT

In continuous preparation of tertiary-butyl hydroperoxide by the direct oxidation of isobutane in dense-phase reaction mixture at a pressure in excess of the critical pressure of the mixture, and under conditions relating to temperature and to oxygen and isobutane content of the mixture, improvement in selectivity to TBHP is realized by a process which comprises conducting a plurality of such oxidation reactions each in one of a series of dense-phase reaction mixtures by continuously introducing isobutane reactant into the first reaction mixture in the series, continuously introducing oxygen reactant into each reaction mixture of the series, and withdrawing a continuous flow from each mixture of the series and introducing this flow into the next mixture of the series, with the provision that the continuous flow withdrawn from the last mixture of the series is taken from the process as a TBHP-containing product mixture characterized by a conversion of the isobutane reactant of between about 3 and 25 percent.

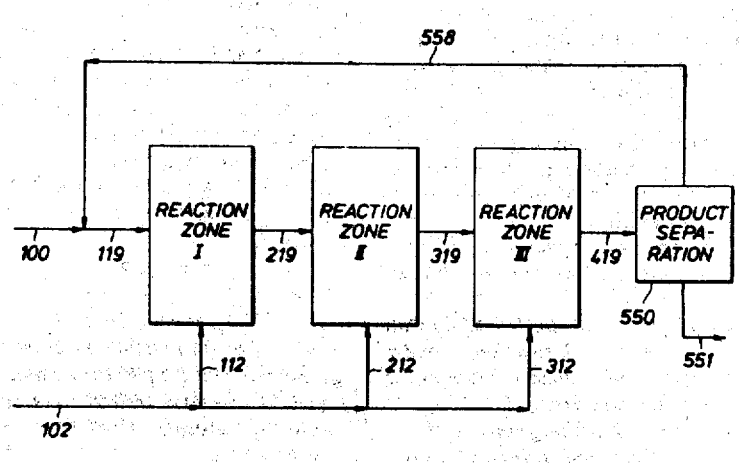

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 9 is cancelled.

Claim 1 is determined to be patentable as amended.

Claims 2–8, dependent on an amended claim, are determined to be patentable.

New claims 10–17 are added and determined to be patentable.

1. In the preparation of tertiary-butyl hydroperoxide by the direct oxidation of isobutane in dense-phase reaction mixture at a reaction temperature in the range from about 140° C. to 170° C. and at a reaction pressure in excess of the critical pressure of the mixture and greater than about 700 psig, the improvement which comprises the steps of:
   (a) conducting a plurality of essentially steady-state isobutane oxidation reactions, each reaction in one of a series of reaction zones, each zone containing an agitated dense-phase oxidation reaction mixture,
   (b) maintaining the reaction mixture of the first zone of the series at a temperature which is in excess of the critical temperature of the mixture, [b] *(c) introducing a continuous flow of isobutane reactant into the mixture of the first zone of the series,*
   [c] *(d)* introducing a continuous flow of oxygen reactant into the mixture of each zone of the series,
   [d] *(e)* withdrawing continuous flows of reaction mixture from each zone of the series, and
   [e] *(f)* introducing each of the withdrawn flows into the mixture of the zone that is next subsequent to the one from which it is withdrawn, with the provision that the flow withdrawn from the last zone of the series is taken from the process as a tertiary-butyl hydroperoxide containing product mixture characterized by a conversion of isobutane of between about 3 and 25 percent.

*10. A process for the preparation of tertiary-butyl hydroperoxide by the direct oxidation of isobutane, which comprises steps for:*
   *(a) conducting a plurality of essentially steady-state isobutane oxidation reactions, each reaction in one of a series of reaction zones, each zone containing an agitated oxidation reaction mixture,*
   *(b) maintaining the oxidation reaction mixture of first zone of the series at a reaction temperature which is in the range of from about 140° C. to 170° C. and which is also in excess of the critical temperature of the mixture and at a reaction pressure in excess of the critical pressure of the mixture and which is also greater than about 700 psig,*
   *(c) maintaining the oxidation reaction mixture of each reaction zone other than the first zone of the series at a reaction temperature which is in the range from about 140° C. to 170° C. and at a reaction pressure which is in excess of the critical pressure of the mixture and which is also greater than about 700 psig,*
   *(d) introducing a continuous flow of isobutane reactant into the mixture of the first zone of the series,*
   *(e) introducing a continuous flow of oxygen reactant into the mixture of each zone of the series,*
   *(f) withdrawing continuous flows of reaction mixture from each zone of the series, and*
   *(g) introducing each of the withdrawn flows into the mixture of the zone that is next subsequent to the one from which it is withdrawn, with the provision that the flow withdrawn from the last zone of the series is taken from the process as a tertiary-butyl hydroperoxide containing product mixture characterized by a conversion of isobutane of between about 3 and 25 percent.*

*11. The process of claim 10, wherein the reaction mixture of each zone (i) contains isobutane in a partial density between about 15 and 35 lb/ft$^3$, (ii) contains oxygen in a concentration between about 0.005 and 5 percent by mol, (iii) has a temperature between about 140° and 170° C., and (iv) has a pressure greater than about 800 psig.*

*12. The process of claim 10, wherein the essentially steady-state oxidation reactions are conducted in a series of from 2 to 8 reaction zones, and wherein the reaction mixture of each zone: (i) contains isobutane in a partial density between about 18 and 30 lb/ft$^3$, (ii) contains oxygen in a concentration between about 0.005 and 5 percent by mol, (iii) has a temperature between about 145° and 165° C., and (iv) has a pressure greater than about 800 psig.*

*13. The process of claim 10, wherein the essentially steady-state oxidation reactions are conducted in a series of from 2 to 6 reaction zones, and wherein the reaction mixture of each zone: (i) contains isobutane in a partial density between about 19 and 25 lb/ft$^3$, (ii) contains oxygen in a concentration between about 0.005 and 5 percent by mol, (iii) has a temperature between about 150° and 160° C., and (iv) has a pressure between about 900 and 1500 psig.*

*14. The process of claim 13, wherein the essentially steady-state oxidation reactions are conducted in a series of from 2 to 4 reaction zones.*

*15. The process of claim 11, wherein the product mixture is characterized by a conversion of isobutane between about 5 and 20 percent.*

*16. The process of claim 12, wherein the product mixture is characterized by a conversion of isobutane between about 7 and 15 percent.*

*17. The process of claim 14, wherein the oxygen concentration in the reaction mixture of each zone is between about 0.1 and 3.5 percent by mol, and wherein the product mixture is characterized by a conversion of isobutane of about 10 percent.*

\* \* \* \* \*